US00PP10239P

United States Patent [19]

Noack

[11] Patent Number: Plant 10,239

[45] Date of Patent: Feb. 17, 1998

[54] GROUND COVER ROSE PLANT NAMED 'FLOWER CARPET APPLEBLOSSOM'

[76] Inventor: Werner Noack, Im Fenne 60, 33334 Gütersloh, Germany

[21] Appl. No.: 635,177

[22] Filed: Apr. 25, 1996

[51] Int. Cl.[6] ..... A01H 5/00

[52] U.S. Cl. ..... Plt./1

[58] Field of Search ..... Plt./1, 2, 5, 7.1, Plt./9, 22, 26, 27

*Primary Examiner*—Howard J. Locker

*Attorney, Agent, or Firm*—Burns, Doane, Swecker & Mathis, L.L.P.

[57] ABSTRACT

A new and distinct variety of ground cover rose plant is provided which forms continuously throughout the season attractive long-lasting pure light pink blossoms. The blossoms tend to open on a reliable basis and to retain their attractiveness upon aging. The new variety exhibits a compact, spreading and overhanging (i.e., long arching) growth habit that renders it suitable for growing as an ornamental ground cover in the landscape. The foliage is glossy and contrasts well with the pure light pink blossoms. The pure light blossom coloration is well retained upon the aging of the blossoms, and petals drop off cleanly as the blossoms mature. The new variety propagates well from cuttings, by the budding of an eye, and by grafting. Excellent resistance to blackspot, mildew, and rust are exhibited.

2 Drawing Sheets

SUMMARY OF THE INVENTION

The new variety of ground cover rose plant of the present invention was discovered in June 1994 at Gütersloh, Germany, as a spontaneous mutation of unknown causation of the 'Flower Carpet' variety (U.S. Plant Pat. No. 7,282) which sometimes is known as the 'Noatraum' variety. The 'Flower Carpet' variety previously was produced by the cross of the 'Immensee' variety (non-patented in the United States) and the 'Amanda' variety (non-patented in the United States). The 'Flower Carpet' variety is marketed under the HEIDETRAUM trademark in Germany, and possesses distinctive deep pink blossoms.

I was attracred to the new variety of the present invention primarily because of its distinctive blossom coloration while it was growing in a cultivated area among many plants of the 'Flower Carpet' cultivar. Had I not discovered and preserved the new plant of the present invention it would have been lost to mankind.

It is found that the new ground cover rose plant possesses the following combination of characteristics:

(a) forms attractive pure light pink medium-sized long-lasting blossoms which tend to open on a reliable basis and to retain their attractiveness upon aging,
(b) exhibits a compact, spreading, and long arching growth habit,
(c) forms attractive glossy foliage that contrasts well with the pure light pink blossoms,
(d) exhibits excellent disease resistance with respect to blackspot, mildew, and rust, and
(e) is particularly suited for growing as attractive ornamentation in the landscape.

The new variety meets the needs of the horticultural industry and can be grown to advantage as decorative ornamentation in parks, gardens, public areas, and residential landscapes.

The new variety of the present invention has been found to readily undergo asexual reproduction in Germany by the use of cuttings, by the budding of an eye, and by grafting. Such asexual reproduction as performed in Germany has shown that the characteristics of the new variety are homogeneous and stable and are strictly transmissible from one generation to another.

The new variety has been named the 'Flower Carpet Appleblossom' variety. The new variety also is known as the 'Noamel' variety in Europe and is being marketed under the SOMMERMELODIE trademark in Europe.

BRIEF DESCRIPTION OF THE PHOTOGRAPHS

The accompanying photographs show as nearly true as it is reasonably possible to make the same, in color illustrations of this character, typical specimens of the new variety while growing in the landscape. The illustrated rose plants were four years of age and were observed during June 1994 while growing outdoors on *Rosa laxa* understock at G ütersloh, Germany, FIG. 1 — illustrates a profusion of blossoms and the foliage of the new variety wherein the buds and blossoms are visible in various stages of opening and the good petal drop character of the new variety is visible as the blossoms mature; and FIG. 2 — illustrates the blossoms of the new variety in greater detail than as illustrated in FIG. 1.

DETAILED DESCRIPTION

Figure 1:
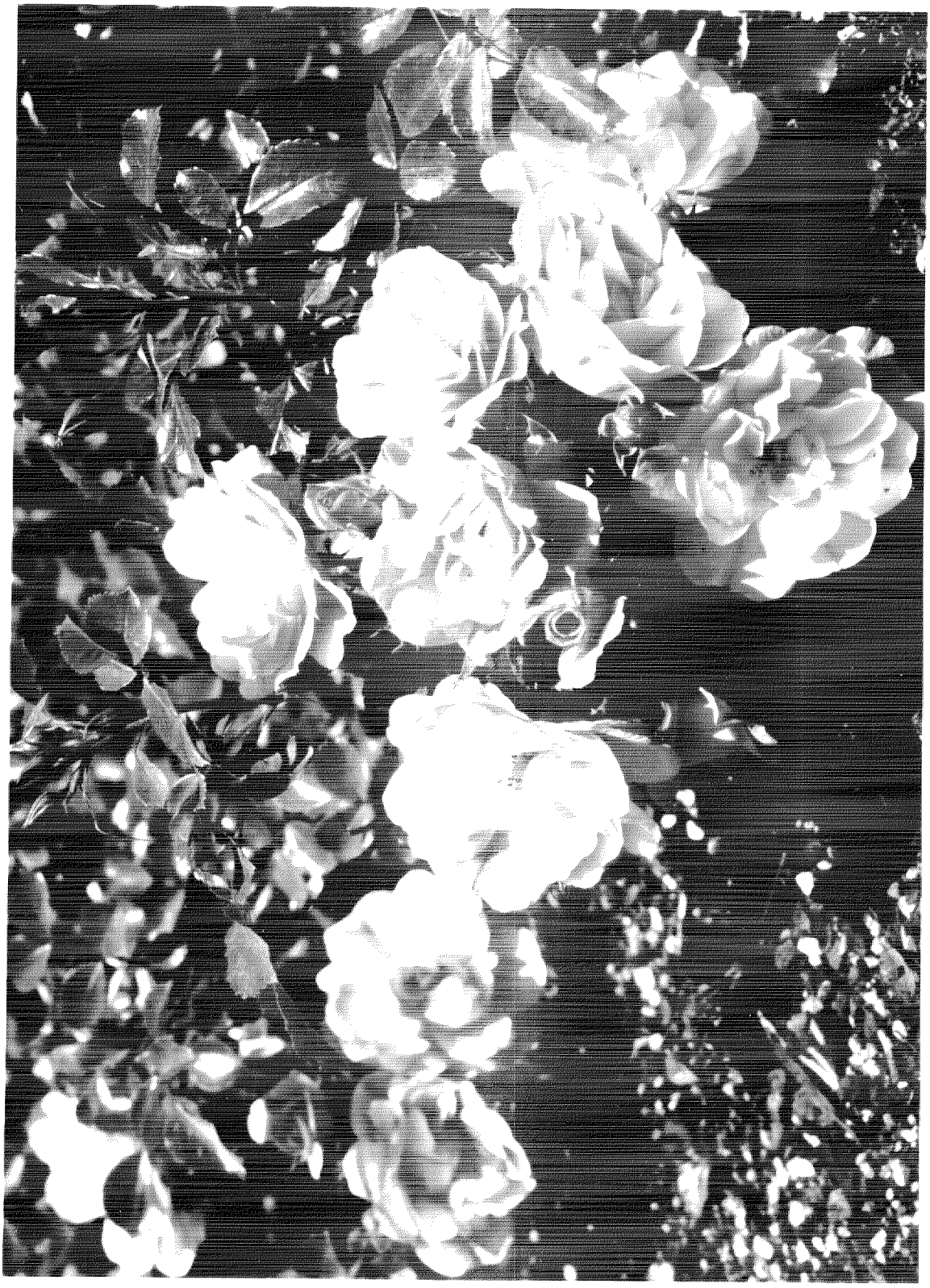
Figure 2:
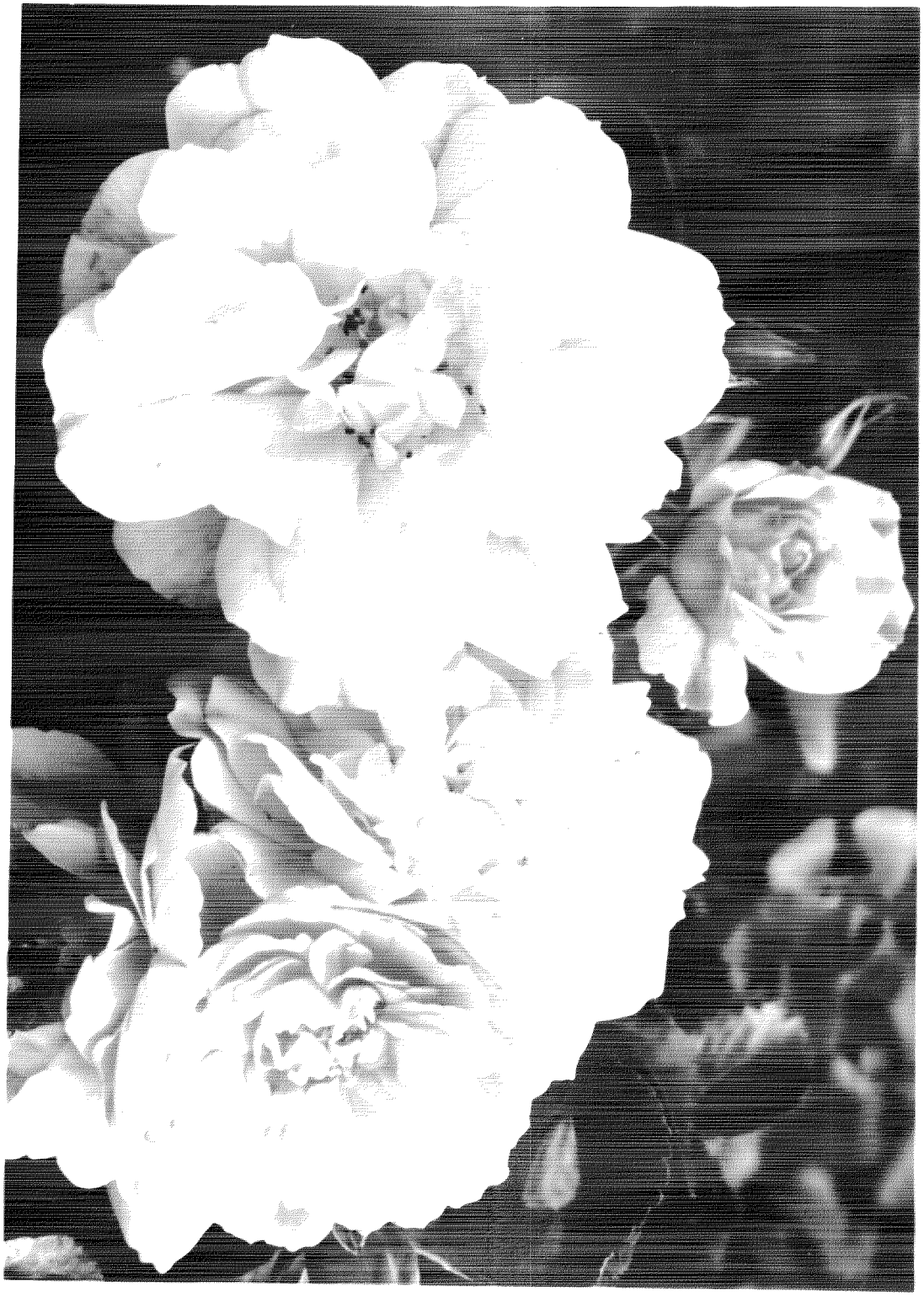

The chart used in the identification of the colors is that of The Royal Horticultural Society (R.H.S. Colour Chart) of London, England. Color terminology in common terms sometimes is included as an aid to the reader. The description is based on the observation of three year-old specimens of the new variety while growing outdoors on *Rosa laxa* understock during July at Gütersloh, Germany.

Class: Ground cover.

Origin: Spontaneous mutation of unknown causation of the 'Flower Carpet' variety (U.S. Plant Pat. No. 7,282).

Plant:

*Height.*—The maximum cane length is approximately 70 to 80 cm. on average at the end of the growing season.

*Form.*—Low, spreading, rounding and overhanging (i.e., long arching), and dense in growth habit that creates an excellent ground cover.

Branches:

*Color.*—Young stems: light green, Green Group 143B, and with a smooth surface. Adult wood: medium green and with a smooth surface.

*Thorns.*—Configuration: average length and slightly curved downward. Frequency: irregular. Color: light yellow in coloration. Greyed-Red Group 179A.

Leaves:

*Stipules.*—Light green, Green Group 143A, in coloration.

*Leaflets.*—Number: commonly 5, and 7, and rarely 9. Quantity: very abundant. Size: small. Serration: simple. Color (young foliage): Upper surface: Green Group 143A. Under surface: slightly lighter green and near Yellow-Green Group 144A. Color (adult foliage): Upper surface: medium green, glossy and approaches Green Group 134B. Under surface: medium green, mat and approaches Green Group 135D. General appearance: dense and glossy. Configuration: oval. Texture: leathery. Petioles: light green in coloration.

Inflorescence:

*Number of flowers.*—Numerous and commonly in large sprays of approximately 6 to 8 blooms each.

*Peduncle.*—Light green in coloration, Green Group 143A, short in length, relatively strong for a ground cover rose, smooth and does not bear prickles, and commonly crooked.

*Sepals.*—Commonly extend beyond the bud and are pointed, approximately 1 cm. in length on average, and Green Group 143A in coloration.

*Buds.*—Shape: rounded. Length: approximately 2 to 3 cm. on average. Size: small. Color when opening: Upper surface: pure light pink, Red-Purple Group 65C to Red-Purple Group 65D. Under surface: light pink and slightly lighter than upper surface.

*Flower.*—Form: slightly cup-shaped, and commonly does not open entirely even upon full maturity. Diameter: small, approximately 3 cm. on average when fully expanded and commonly borne in clusters. Color (when opening begins): Upper surface: pure light pink, Red-Purple Group 65C to Red-Purple Group 65D. Under surface: light pink and slightly lighter than upper surface. Color (when blooming): as above with the exception that a near white area adjacent the point of petal attachment may become at least partially visible. Color (at end of opening): as above with the exception that Red-Purple Group 65D is somewhat more pronounced as the petals lighten particularly toward the blossom centers. Fragrance: slight. Lasting quality: each blossom is long lasting and commonly lasts approximately 3 weeks on plant, and approximately 5 days when cut and placed in a vase. The lives of the blossoms vary somewhat with the month of the year and the environmental conditions that are encountered. Petal form: the edges tend to be relatively straight and substantially even, the shape is elliptical, and the blossom center initially is covered by the petals. Petaloids: commonly few in number. Petal number: under normal growing conditions approximately 15 on average. In some instances 20 or more petals are formed. Petal appearance: satiny on both surfaces. Petal arrangement: generally arranged in a somewhat regular pattern with overlapping edges. Petal texture: average. Petal drop: good with a clean disengagement of the petals upon full maturity. The petals drop well and leave a clean appearance on the plant. This can be termed a self-cleaning character. Stamens: regularly arranged around the styles, and Yellow Group 11A in coloration. Filaments: light yellow in appearance. Pollen: yellow in coloration. Stigmas: yellow in coloration Yellow Group 2D, and almost transparent. Styles: thin, bunched, and tend to be of substantially the same length. Hips: small, round, cupped and green with reddish tint in coloration.

Development:

*Vegetation.*—Vigorous and overhanging.

*Blooming.*—Abundant and substantially continuous throughout the season.

*Winter hardiness.*—Good, when reproduced by the budding of an eye the new variety has withstood a winter temperature of –20° C.

*Resistance to diseases.*—Excellent with respect to blackspot, mildew, and rust.

I claim:

1. A new and distinct variety of ground cover rose plant characterized by the following combination of characteristics:

(a) forms attractive pure light pink medium-sized, long-lasting blossoms which tend to open on a reliable basis and to retain their attactiveness upon aging,
(b) exhibits a compact, spreading, and long arching growth habit,
(c) forms attractive glossy foliage that contrasts well with the pure light pink blossoms,
(d) exhibits excellent disease resistance with respect to blackspot, mildew, and rust, and
(e) is particularly suited for growing as attractive ornamentation in the landscape;

substantially as herein shown and described.

* * * * *

UNITED STATES PATENT AND TRADEMARK OFFICE

CERTIFICATE OF CORRECTION

PATENT NO. : PP 10,239
DATED : February 17, 1998
INVENTOR(S) : Werner Noack

It is certified that error appears in the above-identified patent and that said Letters Patent is hereby corrected as shown below:

Title page,
Item [54], Title, delete "FLOWER CARPET APPLEBLOSSOM" and insert -- 'NOAMEL' --.

Column 1,
Lines 6, 8 and 11, delete, "'Flower Carpet'" and insert -- 'Noatraum' --.
Line 7, delete, "which sometimes is known as the 'Noatraum' variety.".
Line 14, delete, "attracred" and insert -- attracted --.
Line 17, delete, "'Flower Carpet' cultivar" and insert -- 'Noatraum' cultivar --.

Column 2,
Lines 1-2, delete, "'Flower Carpet Appleblossom'" and insert -- 'Noamel' --.
Lines 13-14, delete, "G ütersloh" and insert -- Gütersloh --.
Line 35, delete, "'Flower Carpet'" and insert -- 'Noatraum' --.

Signed and Sealed this

First Day of November, 2005

JON W. DUDAS
*Director of the United States Patent and Trademark Office*